US012220264B2

(12) United States Patent
Acevedo et al.

(10) Patent No.: US 12,220,264 B2
(45) Date of Patent: Feb. 11, 2025

(54) PACKAGING SYSTEM FOR STERILE TRANSFER OF NON-STERILE BATTERY

(71) Applicant: INSURGICAL INC, Austin, TX (US)

(72) Inventors: Richard Acevedo, Austin, TX (US); Philip Tetzlaff, Austin, TX (US)

(73) Assignee: INSURGICAL. INC., Austin, TX (US)

( * ) Notice: Subject to any disclaimer, the term of this patent is extended or adjusted under 35 U.S.C. 154(b) by 23 days.

(21) Appl. No.: 18/081,860

(22) Filed: Dec. 15, 2022

(65) Prior Publication Data

US 2023/0190400 A1 Jun. 22, 2023

Related U.S. Application Data

(60) Provisional application No. 63/290,718, filed on Dec. 17, 2021.

(51) Int. Cl.
*A61B 50/33* (2016.01)
*A61B 50/30* (2016.01)

(52) U.S. Cl.
CPC ...... *A61B 50/33* (2016.02); *A61B 2050/3008* (2016.02); *A61B 2050/314* (2016.02)

(58) Field of Classification Search
CPC . A61B 50/30; A61B 50/33; A61B 2050/0056; A61B 2050/0068; A61B 2050/3008; B65D 75/522
USPC ....... 206/570, 731, 733, 734, 774, 210, 207, 206/305, 349, 470, 363, 779–780, 467, 206/462–463
See application file for complete search history.

(56) References Cited

U.S. PATENT DOCUMENTS

| | | | | |
|---|---|---|---|---|
| 5,037,000 | A * | 8/1991 | Selame | B65D 83/0805 221/302 |
| 6,066,089 | A * | 5/2000 | Costello | A61B 1/00048 600/102 |
| 7,204,367 | B2 * | 4/2007 | Bott | B65D 73/0092 53/430 |
| 8,459,460 | B1 * | 6/2013 | Hansen | B65D 77/0413 206/769 |
| 2005/0247587 | A1 * | 11/2005 | Holland-Letz | B25H 3/003 206/349 |
| 2005/0252822 | A1 * | 11/2005 | Wu | B65D 85/54 206/349 |
| 2016/0106401 | A1 * | 4/2016 | Beardsley | A61B 17/10 606/1 |
| 2016/0192989 | A1 * | 7/2016 | Aman | A61B 50/22 606/53 |
| 2016/0211688 | A1 * | 7/2016 | Orr | A61B 50/39 |
| 2018/0090959 | A1 * | 3/2018 | Orr | H02J 50/10 |
| 2019/0175868 | A1 * | 6/2019 | Spens | A61B 50/30 |
| 2020/0022771 | A1 * | 1/2020 | Chapolini | A61B 50/00 |
| 2022/0338947 | A1 * | 10/2022 | Cancilla | A61B 46/10 |
| 2023/0086331 | A1 * | 3/2023 | Cannon | B65D 75/522 206/307 |

* cited by examiner

*Primary Examiner* — Robert Poon
(74) *Attorney, Agent, or Firm* — CLEARPAT SERVICES, LLC (57) ABSTRACT

A medical device packaging system for securing a sterile medical device, having controlled sterile and non-sterile zones, and features for controlling and maintaining said zones that allow medical personnel to perform a simple and efficient transfer of a non-sterile battery into a sterile powered medical device without compromising the device sterility in a sterile field.

11 Claims, 9 Drawing Sheets

FIG. 9 ns but not otherwise revealed to the page.

PACKAGING SYSTEM FOR STERILE TRANSFER OF NON-STERILE BATTERY

BACKGROUND OF THE INVENTION

This disclosure relates generally to packaging systems for battery-powered medical devices and more particularly to packaging for single use, limited use, sterile, battery-powered medical devices supplied to the operating room without batteries pre-installed in the device.

Important factors for any surgical instrument include sterility, cost of acquisition, maintenance, and reliability during use in the surgical suite. Each of these factors can have a significant impact on the cost of medical care for both the patient and the provider.

In recent years, there has been significant focus on the ever-increasing cost of medical care. These cost increases have led to skyrocketing insurance premiums, reduced coverage, reduced reimbursements, increased fees for services, severe reductions in services for some patient groups by some providers, and unfortunately an apparent increase in infections and medical mishaps.

In an effort to reduce costs and improve profitability, both service providers and medical device suppliers are continuously looking for ways to streamline procedures, reduce time, cost, and risk from their products and services without reducing the quality of the products or services they provide to their customers. One area to benefit from these savings and improvements has been in the orthopedic surgical field through the use of high precision, battery powered surgical instrumentation In recent years, both manufacturers and end-users are requiring longer shelf life and longer battery life in the tools they utilize in the operating room. As a result, manufacturers have begun looking for improved ways to achieve that goal without compromising sterile protocols or adding additional waste.

It has been recognized in recent years that typical re-usable, and sterilizable batteries used in surgical equipment provided by many large instrument providers have a high initial purchase cost and relatively short shelf life in terms of their ability to hold a full charge. As a result, end-users have been demanding better battery systems and lower costs, and instrument providers have been looking for ways to reduce cost and improve reliability by making batteries more efficient with higher energy storage capacity, reduced size, and improved rechargeable lifespans. Unfortunately, some of the proffered solutions come with greater risk of compromised sterility When a non-sterile element such as a battery must be installed internally to a sterile medical device in the operating field, the sterile transfer process is critical to the sterility of the surgical field and safety of the patient. A common situation which requires this activity is the use or exchange of non-sterile batteries utilized in pre-sterilized devices. In addition to contact with a non-sterile element, there exists a principle that anything below any part of a non-sterile person or item in the field is considered non-sterile. All to often the transfer of the battery results in a non-sterile person or object making contact with a sterile component or article, resulting in a breach of sterility. While many methods to accomplish a safe transfer of this type have been explored, most have significant risk of, or fall short of guaranteeing a sterile transfer every time.

SUMMARY OF THE INVENTION

With the recent advent of disposable, single use and limited use medical tool systems, there is a need for devices and methods to ensure a safe transfer of non-sterile batteries into sterile medical devices and tools within a surgical environment.

The present disclosure provides a packaging system and method that secures and controls the medical device in the surgical field, creates controlled sterile and non-sterile zones around the device, and allows the medical staff to do a simple and efficient transfer of a fully charged, reusable or disposable non-sterile battery into a powered medical device while ensuring that sterility is maintained.

A packaging system as disclosed herein can be a packaging system capable of holding a powered medical device, packaged in such a way as to guarantee that the device remains sterile during a simple and safe insertion of a non-sterile or disposable battery, without the risk of inadvertent contact by a non-sterile person or article to any part of the sterile components or exterior of the medical device.

A packaging system as disclosed herein comprises specific sterile and non-sterile zones around the powered medical device that can ensure that a non-sterile battery can only make contact with an internal portion of the battery housing which is ultimately sealed by a sterile exterior cover in such a manner so as to assure that the entirety of the exterior of the powered medical device remains sterile for the subsequent medical procedure for which it is intended.

The packaging system disclosed herein can be implemented for any battery powered medical device, including but not limited to disposable, single use, limited use or fully re-usable, autoclavable tools.

In an aspect, the present disclosure provides a medical device packaging system comprising controlled sterile and non-sterile zones in an assembly; wherein said packaging assembly is releasably secured to a medical device such that a sterile person can handle the sterile medical device and present it to a non-sterile person in a controlled manner within a sterile operating field, wherein said non-sterile person can transfer a non-sterile battery through an opening in the sterile packaging into a battery compartment of the device while the sterile device and an outer sterile battery compartment door remain isolated above and behind a sterility barrier, and wherein a first securing feature of the packaging assembly can be released to expose an opening in the sterile zone of the packaging assembly to remove the device through and from the packaging assembly while maintaining sterility of the overall medical device and the outer sterile battery compartment door behind said opening.

In some embodiments, the medical device packaging system further comprises a plurality of components comprising a tray assembly for securing the medical device in manner which keeps the sterile medical device and a sterile battery cover on one side of a sterile barrier and an opening to an interior battery compartment on the non-sterile side of the sterile barrier; a second securing feature of the tray assembly which captures and shields the exterior battery compartment of the medical device and further shields the medical device by isolating the exterior of the device within the sterile area of the packaging; a releasable sterile barrier shield on the tray assembly configured to open and expose an opening in the tray assembly and the opening to the interior of the battery compartment of the medical device, wherein said openings in the tray assembly and battery compartment allows a non-sterile battery to pass through the openings into the battery compartment; and a further feature which allows the securing function of the tray system to be released and the medical device to be removed backward and upward from the tray assembly toward the sterile field such that the battery compartment door can be closed in a sterile fashion.

In some embodiments of the medical device packaging system, the orientation of the medical device in the tray assembly provides access to the opening of the battery compartment while maintaining the battery housing cover vertically oriented above and behind the releasable sterile barrier shield on the sterile side the shield feature.

In some embodiments, the medical device packaging system further comprises capture features on the tray assembly which capture and contain the battery compartment of a medical device, while allowing access from a non-sterile side of the barrier to insert the non-sterile battery.

In some embodiments, the medical device packaging system further comprises a hinge feature on the releasable sterile barrier shield feature of the tray assembly which allows the tray system to be opened and releasing the captured battery compartment cover, without detaching the shield feature from the tray assembly.

In some embodiments, the medical device packaging system further comprises a compartmental cavity of the tray assembly configured to secure the medical device, having at least one securement feature which extends into the sterile cavity of the tray assembly to secure the battery compartment of the device in place.

In some embodiments, the medical device packaging system further comprises releasable snap features on the tray assembly configured to hold closed a compartment securing the medical device and configured to allow the intentional removal of the medical device by a user.

In some embodiments, the medical device packaging system may alternately comprise a releasable sterile barrier shield feature of the tray assembly, as noted above, which is completely removable.

In some embodiments, the medical device packaging system may alternately comprise a fixed sterile barrier shield feature of the tray assembly, as noted above, which is fully attached to the sterile tray, but configured to strategically flex such that the tool can be removed from the sterile zone above.

In some embodiments, the medical device packaging system further comprises at least one outer sterile barrier to contain the tray assembly and the sterile medical device.

In some embodiments of the medical device packaging system the tray assembly is configured from injection molded materials.

In some embodiments of the medical device packaging system the tray assembly is configured from vacuum formed materials.

In some embodiments of the medical device packaging system the tray assembly is configured from die cut materials.

In another aspect, the present disclosure provides a method of using a medical device packaging system comprising controlled sterile and non-sterile zones in an assembly; wherein said packaging assembly is releasably secured to a medical device such that a sterile person can handle the sterile medical device and present it to a non-sterile person in a controlled manner within a sterile operating field, wherein said non-sterile person outside of the sterile field can transfer a non-sterile battery through an opening in the sterile packaging into a battery compartment of the device while the sterile device and an outer sterile battery compartment door remain isolated above and behind a sterility barrier, and wherein a first securing feature of the packaging assembly can be released to expose an opening in the sterile zone of the packaging assembly to remove the device through and from the packaging assembly while maintaining sterility of the overall medical device and the outer sterile battery compartment door behind said opening following the insertion of the non-sterile battery.

In some embodiments, methods are proposed whereby a sterile end-user can hold a sterile tool body while still secured in a sterile packaging tray assembly in such a manner that a non-sterile person can install a non-sterile battery into an exposed battery housing inner compartment without compromising sterile integrity of the instrument or the surrounding sterile field.

In some embodiments, methods are proposed whereby a sterile end-user can close an exposed battery compartment with a non-sterile battery having been placed therein while a battery-operated tool is secured within a sterile packaging tray assembly, without compromising the sterile integrity of said tool.

Provided herein is a method of sterile transfer of a non-sterile component to a sterile device in a sterile field comprising: providing a medical device packaging system comprising a packaging tray assembly having both sterile and non-sterile zones; providing a sterile medical device releasably secured within a sterile zone of the packaging tray assembly; wherein said medical device comprises a sterile receiver housing and sterile receiver housing cover; providing a non-sterile component configured for assembly to the sterile medical device within the sterile field; inserting said non-sterile component internally into a receiver housing opening of the sterile receiver housing through a non-sterile zone opening in the packaging tray assembly; closing the open receiver housing opening with the sterile receiver housing cover; and removing the sterile tool comprising the internally inserted non-sterile component from the packaging tray assembly in the sterile field.

Provided herein is a method of sterile transfer of a non-sterile component to a sterile device in a sterile field comprising: providing a medical device packaging system comprising a packaging tray assembly having both sterile and non-sterile zones; providing a sterile medical device releasably secured within a sterile zone of the packaging tray assembly; wherein said medical device comprises a sterile receiver housing and sterile receiver housing cover; providing a non-sterile component configured for assembly to the sterile medical device within the sterile field; inserting said non-sterile component internally into a receiver housing opening of the sterile receiver housing through a non-sterile zone opening in the packaging tray assembly; removing the sterile tool comprising the internally inserted non-sterile component from the packaging tray assembly in the sterile field; and closing the open receiver housing opening with the sterile receiver housing cover.

In some embodiments of the method, the non-sterile component is a battery.

In some embodiments of the method, said battery comprises: a disposable battery; a single use battery; a limited use battery; a rechargeable battery; or a recyclable battery.

In some embodiments of the method, the medical device comprises: a reusable power tool; a disposable power tool; a single use power tool or limited use power tool.

In some embodiments of the method, the packaging tray assembly having both sterile and non-sterile zones further comprises providing at least one sterile barrier shield, wherein said barrier shield is: releasable; removeable; hinged; or a combination thereof.

In some embodiments of the method, said sterile barrier shield provides an access port to a non-sterile zone in the packaging tray assembly.

In some embodiments of the method, the packaging tray assembly having both sterile and non-sterile zones further comprises providing at least one sterile barrier shield, wherein said barrier shield is non-releasable; or non-removeable.

In some embodiments of the method, the packaging tray assembly having both sterile and non-sterile zones further comprises providing retaining features within the sterile zone to releasably secure the sterile medical device during the insertion of said non-sterile component internally into the receiver housing opening of the sterile receiver housing.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein) of which:

The foregoing and other features of the present disclosure will become apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

DETAILED DESCRIPTION OF THE INVENTION

While various embodiments of the present invention have been shown and described herein, it will be obvious to those skilled in the art that such embodiments are provided by way of example only. Numerous variations, changes, and substitutions may now occur to those skilled in the art without departing from the invention. It should be understood that various alternatives to the embodiments of the present disclosure described herein may be employed.

As used herein, and unless otherwise specified, the term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 30%, 25%, 20%, 15%, 10%, 9%, 8%, 7%, 6%, 5%, 4%, 3%, 2%, 1%, 0.5%, 0.1%, or 0.05% of a given value or range. In certain embodiments, the term "about" or "approximately" means within 40.0 mm, 30.0 mm, 20.0 mm, 10.0 mm 5.0 mm 1.0 mm, 0.9 mm, 0.8 mm, 0.7 mm, 0.6 mm, 0.5 mm, 0.4 mm, 0.3 mm, 0.2 mm or 0.1 mm of a given value or range. In certain embodiments, the term "about" or "approximately" means within 5.0 kg, 2.5 kg, 1.0 kg, 0.9 kg, 0.8 kg, 0.7 kg, 0.6 kg, 0.5 kg, 0.4 kg, 0.3 kg, 0.2 kg or 0.1 kg of a given value or range, including increments therein. In certain embodiments, the term "about" or "approximately" means within 1 hour, within 45 minutes, within 30 minutes, within 25 minutes, within 20 minutes, within 15 minutes, within 10 minutes, within 5 minutes, within 4 minutes, within 3 minutes within 2 minutes, or within 1 minute. In certain embodiments, the term "about" or "approximately" means within 20.0 degrees, 15.0 degrees, 10.0 degrees, 9.0 degrees, 8.0 degrees, 7.0 degrees, 6.0 degrees, 5.0 degrees, 4.0 degrees, 3.0 degrees, 2.0 degrees, 1.0 degrees, 0.9 degrees, 0.8 degrees, 0.7 degrees, 0.6 degrees, 0.5 degrees, 0.4 degrees, 0.3 degrees, 0.2 degrees, 0.1 degrees, 0.09 degrees. 0.08 degrees, 0.07 degrees, 0.06 degrees, 0.05 degrees, 0.04 degrees, 0.03 degrees, 0.02 degrees or 0.01 degrees of a given value or range, including increments therein.

As used herein, and unless otherwise specified, the term "plurality", and like terms, refers to a number (of things) comprising at least one (thing), or greater than one (thing), as in "two or more" (things), "three or more" (things), "four or more" (things), etc.

As used herein, the terms "connected", "operationally connected", "coupled", "operationally coupled", "operationally linked", "operably connected", "operably coupled", "operably linked," and like terms, refer to a relationship (mechanical, linkage, coupling, etc.) between elements whereby operation of one element results in a corresponding, following, or simultaneous operation or actuation of a second element. It is noted that in using said terms to describe inventive embodiments, specific structures or mechanisms that link or couple the elements are typically described. However, unless otherwise specifically stated, when one of said terms is used, the term indicates that the actual linkage or coupling may take a variety of forms, which in certain instances will be readily apparent to a person of ordinary skill in the relevant technology.

As used herein, the terms "comprises". "comprising", or any other variation thereof, are intended to cover a nonexclusive inclusion, such that a process, method, article, or apparatus that comprises a list of elements does not include only those elements but may include other elements not expressly listed or inherent to such process, method, article, or apparatus.

As used herein, whenever the term "at least," "greater than," or "greater than or equal to" precedes the first numerical value in a series of two or more numerical values, the term "at least," "greater than" or "greater than or equal to" applies to each of the numerical values in that series of numerical values. For example, greater than or equal to 1, 2, or 3 is equivalent to greater than or equal to 1, greater than or equal to 2, or greater than or equal to 3.

As used herein, whenever the term "no more than," "less than," or "less than or equal to" precedes the first numerical value in a series of two or more numerical values, the term "no more than," "less than," or "less than or equal to" applies to each of the numerical values in that series of numerical values. For example, less than or equal to 3, 2, or 1 is equivalent to less than or equal to 3, less than or equal to 2, or less than or equal to 1.

As used herein, the terms "user", "end user" or "end-user" are interchangeably used. As used herein, and unless otherwise specified, these terms refer to a person or customer who ultimately uses or is intended to ultimately use a product. End users may or may not be "customers" in the usual sense-they are commonly employees of the customer. For example, if a large retail corporation buys a software package for its employees to use, even though the large retail corporation was the "customer" which purchased the software, the end users are the employees of the company, who will use the software at work. In an alternate example, hospitals which purchase power tools and medical devices for its employees (doctors and nurses) to use, even though the hospital was the "customer" which purchased the power tools and medical devices, the end users are the employees of the hospital, who will use the power tools and medical devices in surgery.

As used herein, the terms "subject" or "patient" are used interchangeably. As used herein, the terms "subject" and "subjects" refers to an animal (e.g., birds, reptiles, and mammals), preferably a mammal including a primate (e.g., a monkey, chimpanzee, and a human) (and a non-primate (e.g., a camel, donkey, zebra, cow, pig, horse, cat, dog, rat, and mouse). In some embodiments, the mammal is 0 to 6 months old, 6 to 12 months old, 1 to 5 years old, 5 to 10 years old, 10 to 15 years old, 15 to 20 years old, 20 to 25 years old, 25 to 30 years old, 30 to 35 years old. 35 to 40 years old. 40 to 45 years old, 45 to 50 years old, 50 to 55 years old, 55 to 60 years old, 60 to 65 years old, 65 to 70 years old, 70 to 75 years old, 75 to 80 years old, 80 to 85 years old, 85 to 90 years old. 90 to 95 years old, 95 to 100 years old or over 100 years old. In a preferred embodiment, the subject or patient is a human. In certain embodiments, the human is 0 to 6 months old, 6 to 12 months (1 year) old, 1 to 10 years old, 10 to 20 years old, 20 to 30 years old, 30 to 40 years old. 40 to 50 years old. 50 to 60 years old, 60 to 70 years old, 70 to 80 years old, 80 to 90 years old, or 90 to 100 years old, 100 to 110 years old, etc., etc. The upper limit of the natural lifespan or maximum lifespan of a human is generally accepted to be about 125 years but is not intended herein to be an upper limit of the age of a patient.

As used herein, and unless otherwise specified, the term "anterior" refers to human anatomy and means the front surface of the body; often used to indicate the position of one structure relative to another, that is, situated nearer the front part of the body. Alternately, it may also refer in a similar fashion to an apparatus or structure.

As used herein, and unless otherwise specified, the term "posterior" refers to human anatomy and means the back surface of the body; Often used to indicate the position of one structure relative to another, that is, nearer the back of the body. Alternately, it may also refer in a similar fashion to an apparatus or structure.

As used herein, and unless otherwise specified, the term "superior" refers to human anatomy and means situated nearer the vertex of the head in relation to a specific reference point; opposite of inferior. It may also mean situated above or directed upward. Alternately, it may also refer in a similar fashion to an apparatus or structure.

As used herein, and unless otherwise specified, the term "inferior" refers to human anatomy and means situated nearer the soles of the feet in relation to a specific reference point; opposite of superior. It may also mean situated below or directed downward. Alternately, it may also refer in a similar fashion to an apparatus or structure.

As used herein, and unless otherwise specified, the term "medial" refers to human anatomy and means situated toward the median plane or midline of the body. Alternately, it may also refer in a similar fashion to an apparatus or structure.

As used herein, and unless otherwise specified, the term "lateral" refers to human anatomy and means denoting a position farther from the median plane or midline of the body or a structure. It may also mean "pertaining to a side". Alternately, it may also refer in a similar fashion to an apparatus or structure.

As used herein, the term "proximity" means nearness in space or relationship, but not excluding the potential to be touching. Proximity is also alternatively meant to mean that one thing may be so close to another thing as to be "in direct or nearly direct contact" (in proximity) with another thing along some point. To "place something in proximity" is also meant to mean that items are "paired" or "mated together" either in their paired function or at some point of contact.

As used herein, and unless otherwise specified, the term "translucent" means allowing some, but not all, light to pass through a thing. Being of a nature that allows for the partial transmission of light bat causing sufficient diffusion to prevent perception of distinct images therethrough. Alternatively, translucent may also mean allowing light to pass through only partially or diffusely; being semi-transparent. In some embodiments, it may be advantageous to modify the meaning of transparent wherein an alternative meaning may include translucent or shaded to mean that the clarity remains only slightly altered or dulled, but the "brightness", "tone", "luminance", "luminosity", and or "lightness" may be altered, allowing filtered light to pass through such as for example may occur with packaging.

As used herein, and unless otherwise specified, the term "vertical", "vertically oriented" and similar terms mean; generally perpendicular to, at, or near, right angles to a horizontal plane; in a direction or having an alignment such that the top of a thing is above the bottom. In certain embodiments, the term "vertically oriented" means within ±20.0 degrees, ±15.0 degrees, ±10.0 degrees, ±9.0 degrees, ±8.0 degrees, ±7.0 degrees, ±6.0 degrees, ±5.0 degrees, ±4.0 degrees, ±3.0 degrees, ±2.0 degrees, ±1.0 degrees, ±0.9 degrees, ±0.8 degrees, ±0.7 degrees, ±0.6 degrees, ±0.5 degrees, ±0.4 degrees, ±0.3 degrees, ±0.2 degrees or ±0.1 degrees of a given value or range, including increments therein.

As used herein, and unless otherwise specified, the term "horizontally oriented" and similar terms mean; generally perpendicular to, at, or near, right angles to a vertical plane; in a direction, or having an alignment such that the top of a thing is generally on, or near the same plane as the bottom, both being parallel or near parallel to the horizon. In certain embodiments, the term "horizontally oriented" means within ±20.0 degrees, ±15.0 degrees, ±10.0 degrees, ±9.0 degrees, ±8.0 degrees, ±7.0 degrees, ±6.0 degrees, ±5.0 degrees, ±4.0 degrees, ±3.0 degrees, ±2.0 degrees, ±1.0 degrees, ±0.9 degrees, ±0.8 degrees, ±0.7 degrees, ±0.6 degrees, ±0.5 degrees, ±0.4 degrees, ±0.3 degrees, ±0.2 degrees or ±0.1 degrees of a given value or range, including increments therein.

As used herein, and unless otherwise specified, the term "substantially perpendicular" and similar terms mean generally at or near 90 degrees to a given line, or surface or to the ground. In certain embodiments, the term "substantially perpendicular" means within ±20.0 degrees, ±15.0 degrees, ±10.0 degrees, ±9.0 degrees, ±8.0 degrees, ±7.0 degrees, ±6.0 degrees, ±5.0 degrees, ±4.0 degrees, ±3.0 degrees, ±2.0 degrees, ±1.0 degrees, ±0.9 degrees, ±0.8 degrees, ±0.7 degrees, ±0.6 degrees, ±0.5 degrees, ±0.4 degrees, ±0.3 degrees, ±0.2 degrees or ±0.1 degrees of a given value or range, including increments therein.

As used herein, and unless otherwise specified, the term "power tool", and similar terms refers to any type of battery-powered instrument commonly found in a hospital surgical setting. These may include, but are not limited to saws, drills, reamers, burring tools, cautery instruments, illuminating instruments, surgical robots and robotic tool accessories. This is not intended to be an exhaustive list, but merely an illustrative listing for the potential applications of this device and methods.

As used herein, and unless otherwise specified, combinations such as "at least one of A, B, or C," "one or more of A, B, or C," "at least one of A, B, and C," "one or more of A, B, and C," and "A, B, C, or any combination thereof" include any combination of A, B, and/or C, and may include multiples of A, multiples of B, or multiples of C. Specifically, combinations such as "at least one of A, B, or C," "one or more of A, B, or C," "at least one of A, B, and C," "one or more of A, B, and C," and "A, B, C, or any combination thereof" may be A only, B only, C only, A and B, A and C, B and C, or A and B and C, where any such combinations may contain one or more member or members of A, B, or C.

As used herein, and unless otherwise specified, the terms "battery cover", "battery door", "battery housing cover", "battery compartment cover" or "battery cover (door)" and like terms refer to the same item and have the same meaning. The battery cover is a moveable feature, usually hinged, that functions to enclose the battery within the sterile battery housing compartment of the device.

As used herein, and unless otherwise specified, the terms "Controlled Sterile and Non-Sterile Zones" refer to sterile zones within the packaging assembly, and specifically within the tray assembly within the packaging assembly. In particular "Controlled Sterile Zones" are protected sterile zones within the tray assembly that are sterile when removed from the packaging assembly and remain sterile when transferred to the surgical field. "Controlled Non-Sterile Zones" are also protected sterile zones within the tray assembly that are sterile when removed from the packaging assembly but become non-sterile after insertion of a non-sterile battery into the product while it is still in the tray assembly. For example, the interior battery compartment is a "controlled non-sterile zone", wherein it is initially sterile within the tray assembly, but becomes non-sterile after a sterility barrier shield is retracted and a non-sterile battery is inserted into the interior battery compartment. The entire tool remains sterile, however, since the sterile exterior battery cover which is in the "controlled sterile zone", is subsequently closed over the interior battery compartment and non-sterile battery, thus maintaining overall sterility of the (exterior) tool.

Figure 1:
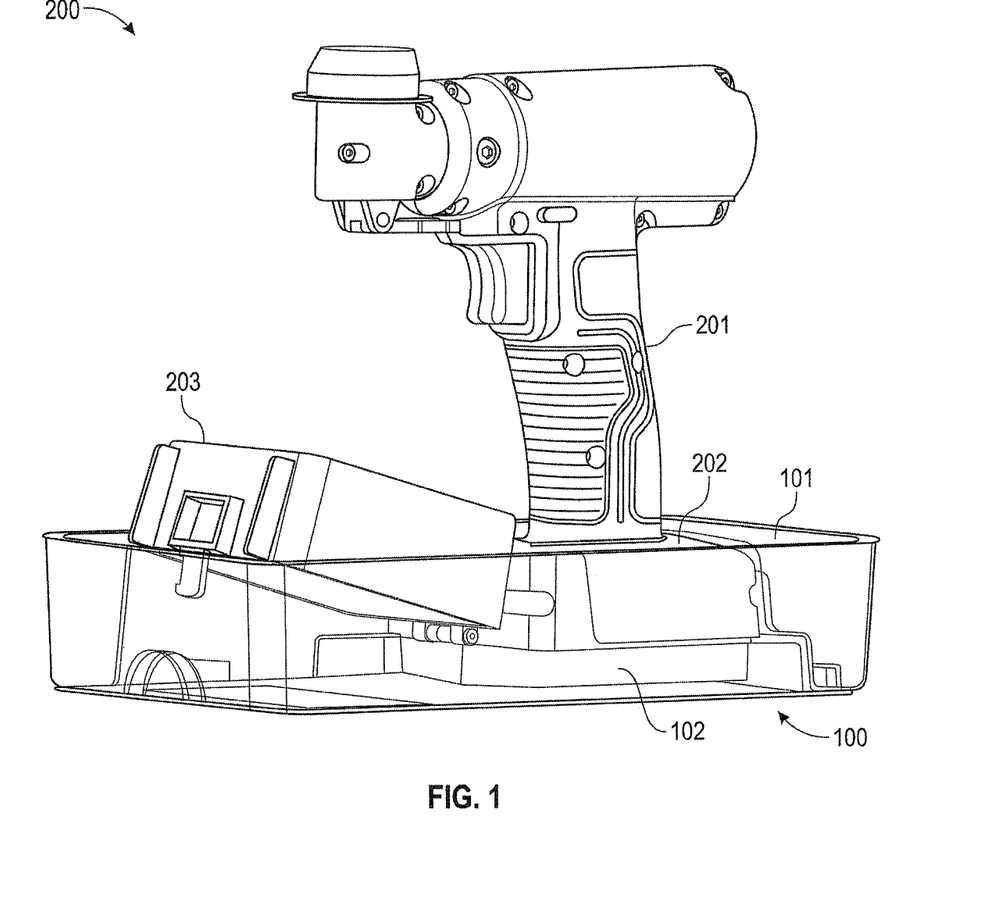
FIG. 1 is a front ISO view of the packaging tray assembly, illustrating the packaging tray assembly after removal from it's outer sterile packaging, with a sterile power tool and open battery compartment cover in the sterile zone behind a releasable (bottom) sterile barrier shield.

A medical device packaging tray assembly 100 is illustrated in FIG. 1, as it would appear following removal from an outer sterile shield "bag" 130, (not shown) and includes sterile zones 101 and non-sterile zones 102 integrated within the assembly. A sterile battery powered medical instrument device 200 is securely positioned within the proximal sterile zones 101, the instrument 200 comprising a device body and handle 201, a proximal battery housing 202 and battery housing cover (door) 203 in an opened position.

Figure 2:
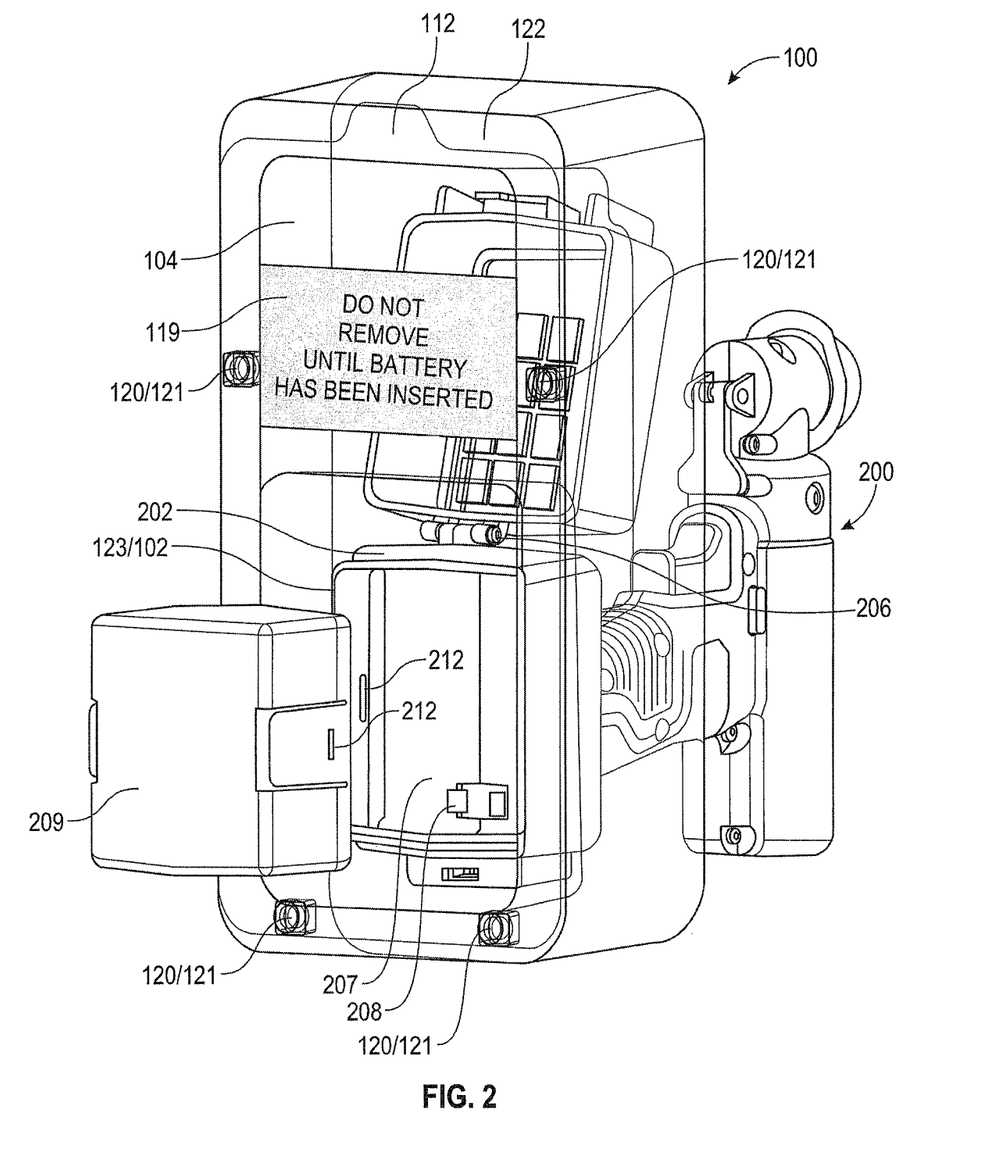
FIG. 2 is a bottom ISO view of FIG. 1, illustrating the non-sterile zone of the packaging tray assembly which is exposed through the releasable (bottom) sterile barrier shield for insertion of a non-sterile battery, wherein the entire exterior of the power tool and battery compartment cover is completely shielded and held in place within the upper tray portion of the assembly and behind the releasable (bottom) sterile barrier shield.

FIG. 2 illustrates the inferior side of the medical device packaging assembly 100, positioned in a vertically oriented position, as it would be held by a sterile user in a sterile surgical field, prior to inserting a non-sterile battery 209. In the vertical orientation as shown, a releasable sterility barrier shield 104 with a cautionary label 119 is visible to a non-sterile observer, who would presumably be delivering the non-sterile battery 209 to the device, for insertion into the exposed internal battery compartment 207 of the battery housing 202, which is exposed via an opening 123 in the inferior side of the packaging tray assembly 100, which constitutes a non-sterile zone 102 once the tray assembly and instrument are removed from the outer sterile shield "bag" 130, (not shown).

Further, as seen in FIG. 2, the releasable sterility barrier shield 104 comprises a pull tab 112 on one end and a plurality of optional retaining features 120, which are captured in an equal number of retaining captures 121 on the inferior surface 122 of the tray assembly.

Figure 7A:
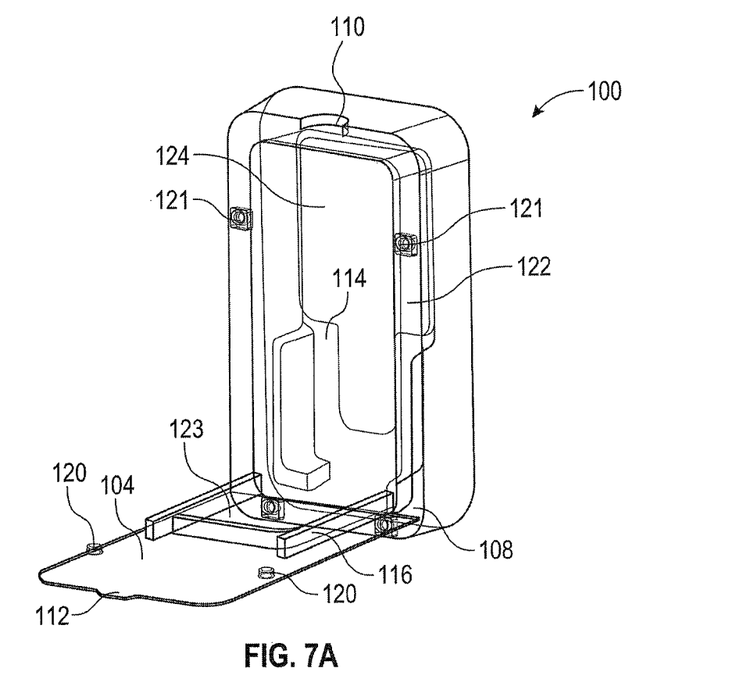
FIG. 7A is an alternate (bottom) ISO view of FIG. 2, illustrating the packaging tray assembly, without a tool and further comprising an optional hinged sterile barrier shield in an opened configuration.
Figure 7B:
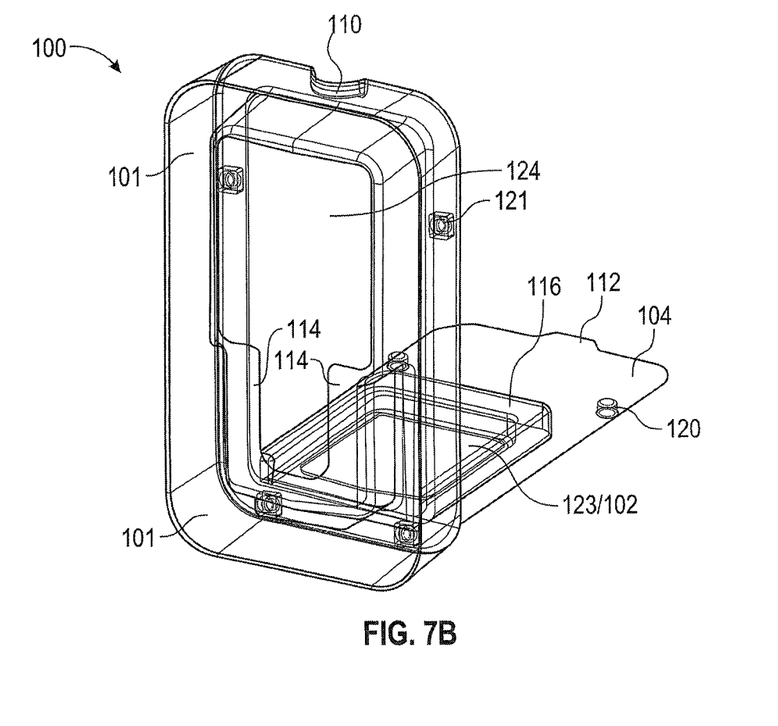
FIG. 7B is an opposite (top) ISO view of FIG. 7A illustrating the packaging tray assembly, without a tool, comprising the optional hinged sterile barrier shield in an opened configuration.
Figure 8:
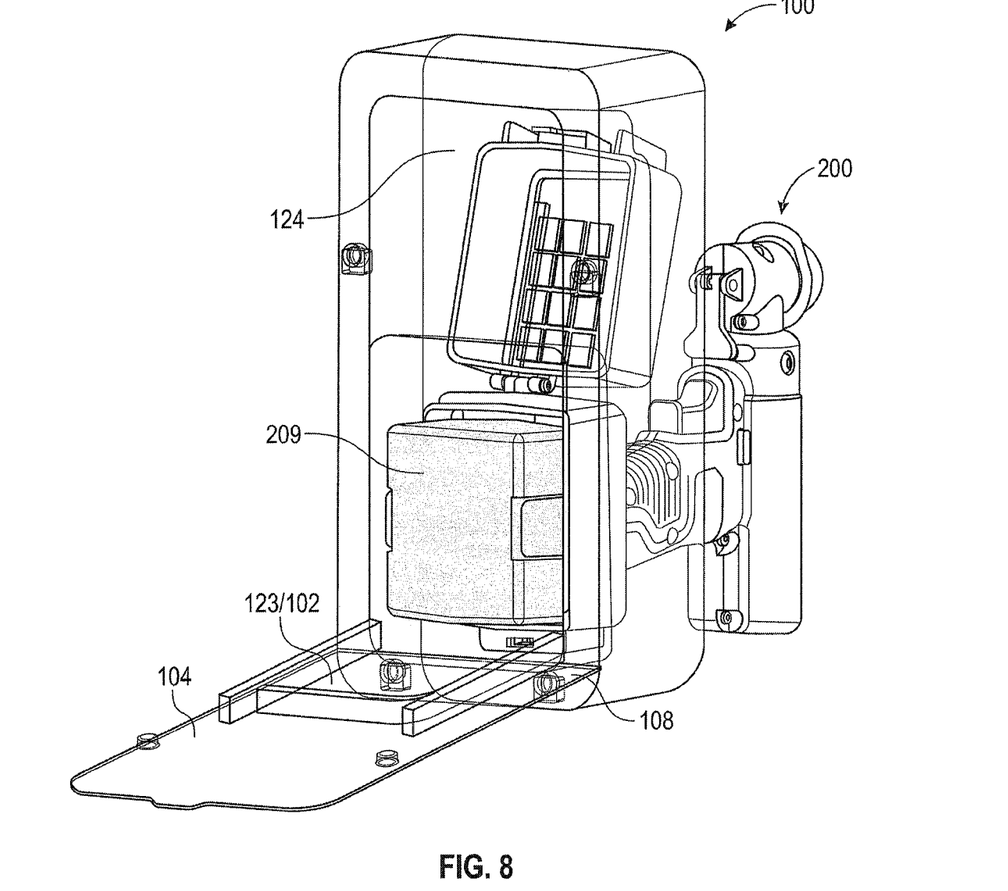
FIG. 8 is a further ISO view of FIG. 7A, illustrating the packaging tray assembly with a tool following insertion of a non-sterile battery in the tool battery compartment and the optional hinged sterile barrier shield in an opened configuration.

Alternately, as seen in FIGS. 7A, 7B & 8, the releasable sterility barrier shield 104 may comprise a pull tab 112 on one end and a plurality of optional retaining features 120, which are captured in an equal number of retaining captures 121 on the inferior surface 122 of the tray assembly.

Further, as seen in FIG. 2, a non-sterile battery 209 is illustrated as it would be oriented for delivery into the exposed internal battery compartment 207 of the battery housing 202, exposed via the non-sterile zone 102 opening 123 in the inferior side of the packaging tray assembly 100. A sterile end-user would present the vertically oriented device in the packaging tray while a presumably non-sterile support person would proceed to properly orient and insert the non-sterile battery 209 into the exposed internal battery compartment 207 of the battery housing 202 until the battery contacts 208 and battery latching mechanism 212 are engaged to secure the battery in the battery housing.

Figure 3:
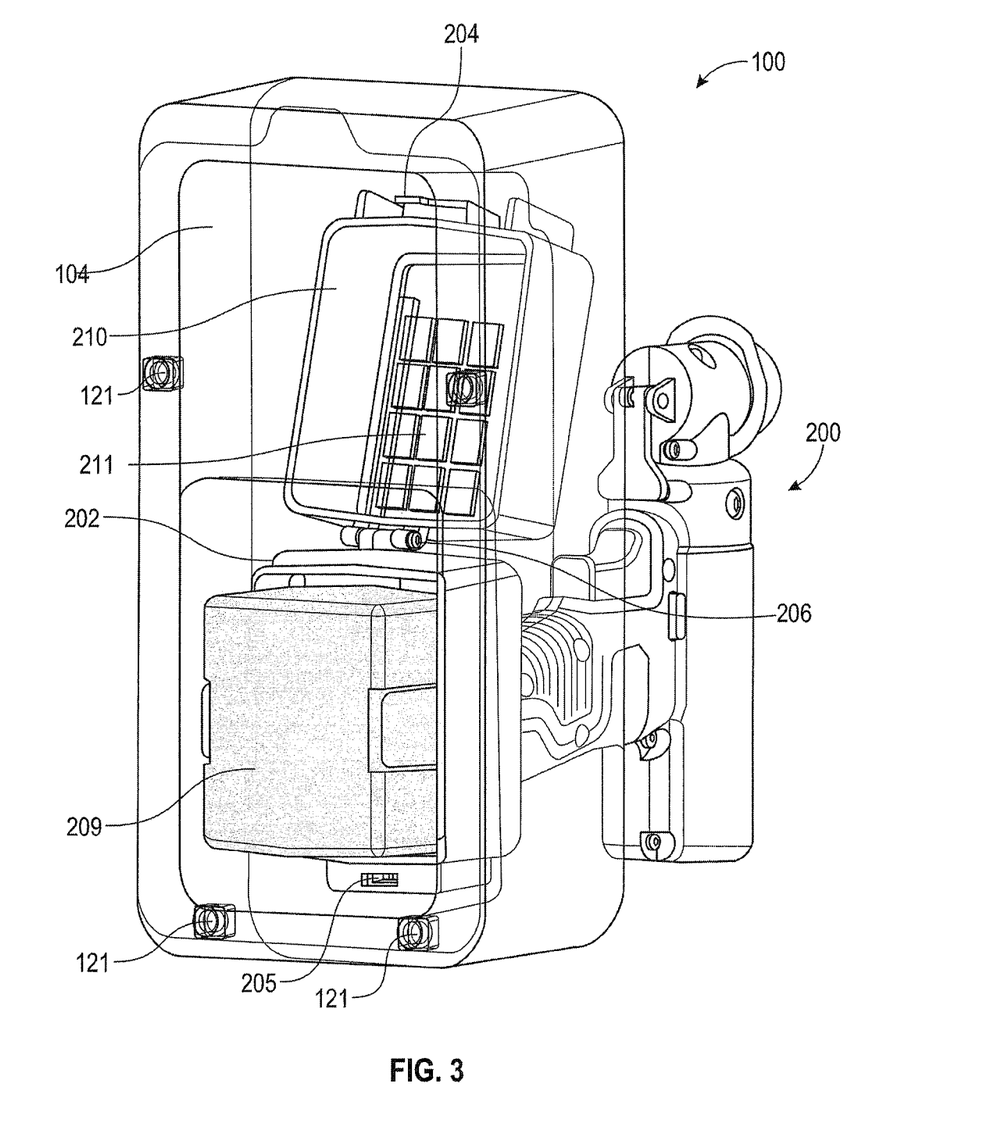
FIG. 3 is a further ISO view of FIG. 2, illustrating the packaging tray assembly following removal of the sterile barrier shield by a non-sterile person, after secure insertion of the non-sterile battery completely within the inner battery compartment.

FIG. 3 illustrates the inferior side of the medical device packaging assembly 100, positioned in a vertical orientation, as it would be held by a sterile user in a sterile surgical field, following insertion of a non-sterile battery 209, and removal or release of the releasable sterility barrier shield 104 with a cautionary label 119. It should be noted at this point that no sterility compromise of the exterior surfaces of the medical device could occur at this point since only the internal compartment 207 of the battery housing has been exposed to the non-sterile battery 209 while the remainder of the entire device has been behind the sterility barrier shield 104 and within the sterile zone 101 of the medical device packaging assembly 100. Also shown in this figure are the interior of the battery housing cover 210 and the battery housing compression pads 211, used to secure the battery snugly within the battery housing and dampen any potential vibration that may occur between the battery and the housing when the device is running FIG. [4] 4A illustrates a key component of the device and method, wherein the vertical orientation positioning of the medical device, as it would be held by a sterile person when next removing the battery laden device 200 from the packaging tray assembly 100. As illustrated herein, a sterile end-user would proceed to remove the battery laden device 200 from the packaging tray by, releasing the capture feature 118 (shown in FIGS. 6A & 6B) and the battery housing male locking latch 204 retaining the battery housing cover 203 and the device 200 within the superior and inferior slide captures 114/116 within the sterile zone 101 and sliding the device vertically upward (proximally) toward the inferior tray opening 124 and back toward the end-user, out of the tray, leading with the open battery housing cover (door) 203. Capture features, as described herein may comprise various forms of snaps and snap retainers, magnets, tape, releasable adhesive (glue), or serrated material (tear away) strips. In the preferred embodiment, snap features interfacing between the releasable components of the tray are used.

Figure 4A:
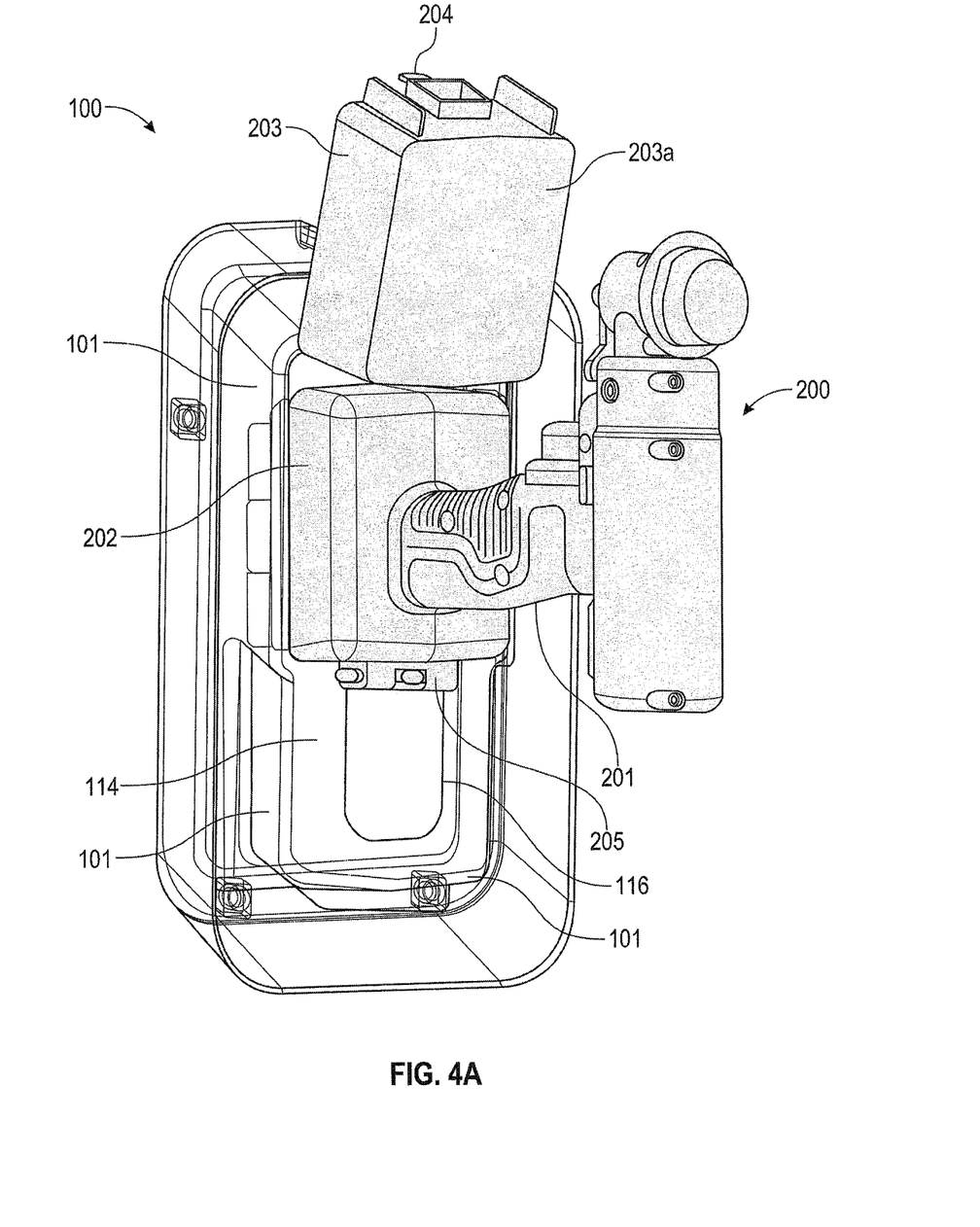
FIG. 4A is a top ISO view of the packaging tray assembly following insertion of the non-sterile battery in the battery compartment and one potential sequence for removal of the tool from the packaging tray. With this possible sequence, the sterile user releases the capture feature(s) holding in the power tool stationary in the packaging tray and slides the power tool up and back, away from the packaging tray. With the power tool now removed from the packaging tray in the same vertical position, a sterile user holding the tool, can now push the hinged battery compartment cover closed, from the top sterile surface of the battery compartment cover, engaging the locking feature of the cover, without making contact with any non-sterile surfaces or items.

Once free of the packaging tray, the sterile end-user can easily push the exterior cover surface (203*a*) of the battery housing cover (door) 203, to pivot the cover about the battery housing hinge 206 and engage the battery hosing locking latch 204 on the cover with the battery housing latch receiver 205 in the external battery housing 202.

Figure 5:
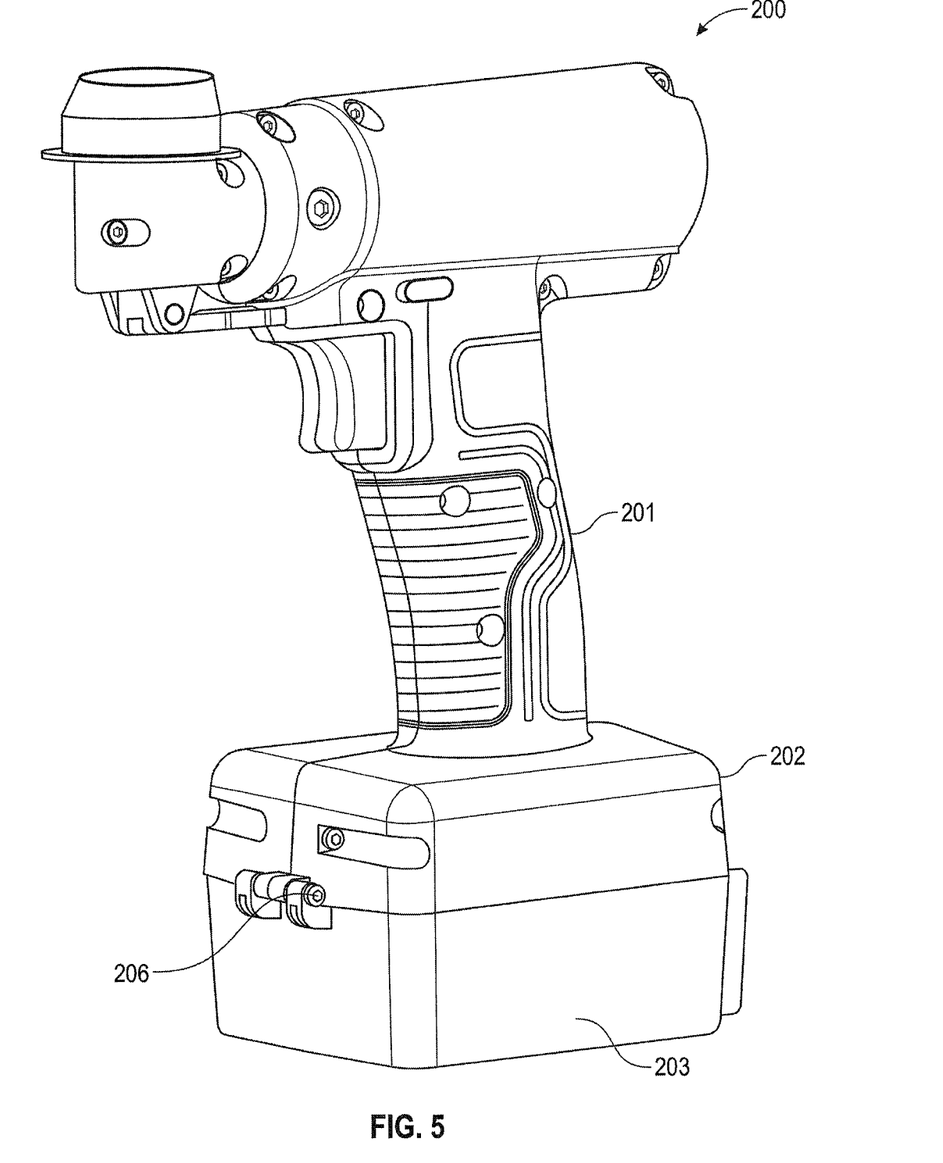
FIG. 5 is a front ISO view of an illustrative sterile power tool following insertion of a non-sterile battery within a sterile field and removal from the packaging tray assembly.

FIG. 5 illustrates an embodiment of a typical medical device assembly 200 as illustrated in FIG. 1, as it would appear following insertion of a non-sterile battery, closure of the battery housing cover and removal from the packaging tray assembly. A sterile battery powered medical instrument device 200 is at this point fully prepped and ready for use.

Figure 6A:
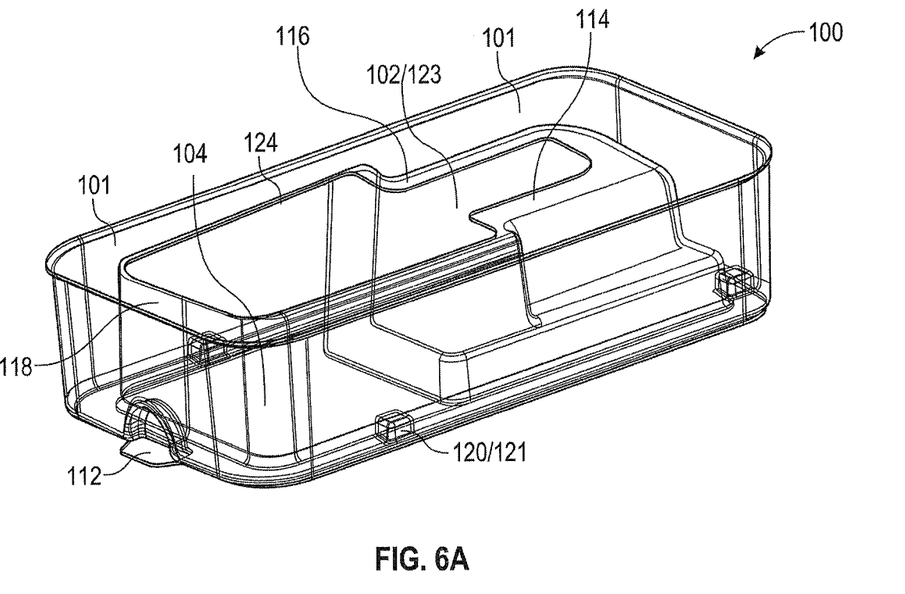
FIG. 6A is a (top) ISO view of the packaging tray assembly, illustrated without a tool.
Figure 6B:
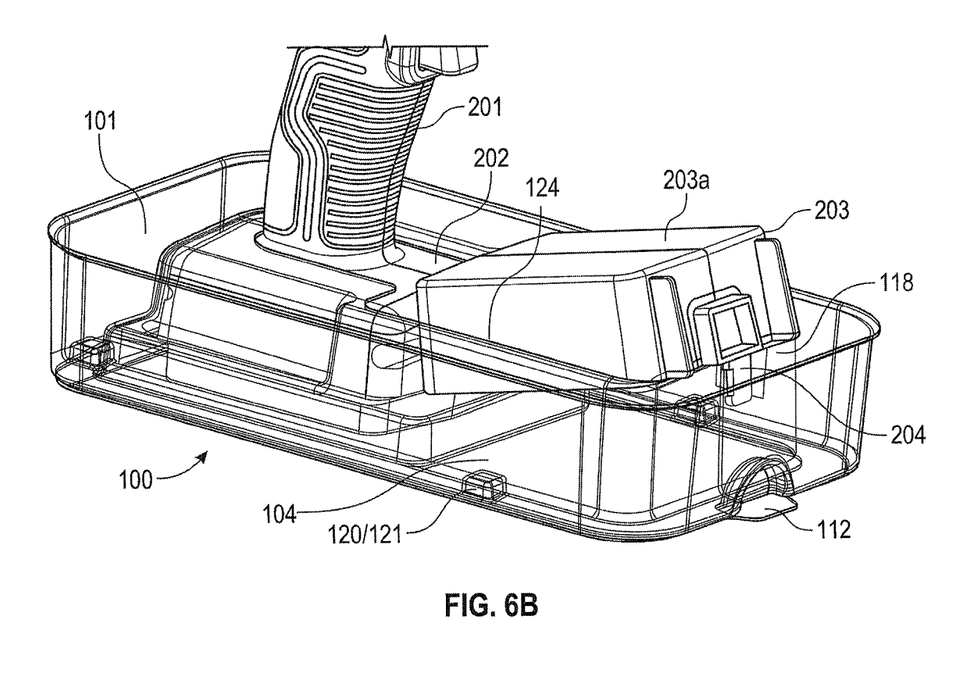
FIG. 6B is an opposite side top ISO view of FIG. 6A with a captured tool body, illustrating placement of the tool body in the slide captures and the open battery compartment door captured within the sterile zone of the packaging tray.

FIG. 6A illustrates an embodiment of a translucent or clear packaging tray assembly 100, in a top ISO view, without a device. As illustrated herein, the proximal, sterile zones 101, comprise capture features, 114/116, 118 for securely retaining the medical device proximal to the inferior non-sterile zone 102, beneath the device. Further, as shown in FIG. 6B, in an opposite side, top IOS view, the representative battery powered tool is nested within the superior and inferior slide captures 114/116, and the battery housing male locking latch is captured on the capture lip 118 of the packaging tray, within the sterile zone 101, above the sterile barrier shield 104.

As noted above, FIGS. 7A & 7B illustrate at least one possible alternative configuration of the releasable sterility barrier shield 104 which may comprises a pull tab 112 on one end, a plurality of optional retaining features 120, which are captured in an equal number of retaining captures 121 on the inferior surface 122 of the tray assembly 100 and a releasable sterility barrier shield hinge feature 108, configured for attachment to one end of the inferior surface 122 of the tray assembly, opposite the pull tab 112. Further, as seen in these figures, pull tab feature 112 is configured to be positioned and grasped within a clearance feature, such as 110, in the tray assembly 100. Alternatively, the sterility barrier shield hinge feature 108 may also comprise a tape-like hinge versus a flexible plastic hinge. This feature, would potentially prevent the releasable sterility barrier shield 104 from accidentally dropping into the sterile field when it is released and contaminating the field.

FIG. 8 is an illustrative view of FIG. 7A with a device, nested in the packaging tray with a hinged sterile barrier shield, following insertion of the battery, before removal of the tool in an upward and backward fashion relative to the tray, maintaining the battery housing cover 203 in the sterile zone, behind the sterile shield 104, prior to closure of the battery housing cover.

Figure 9:
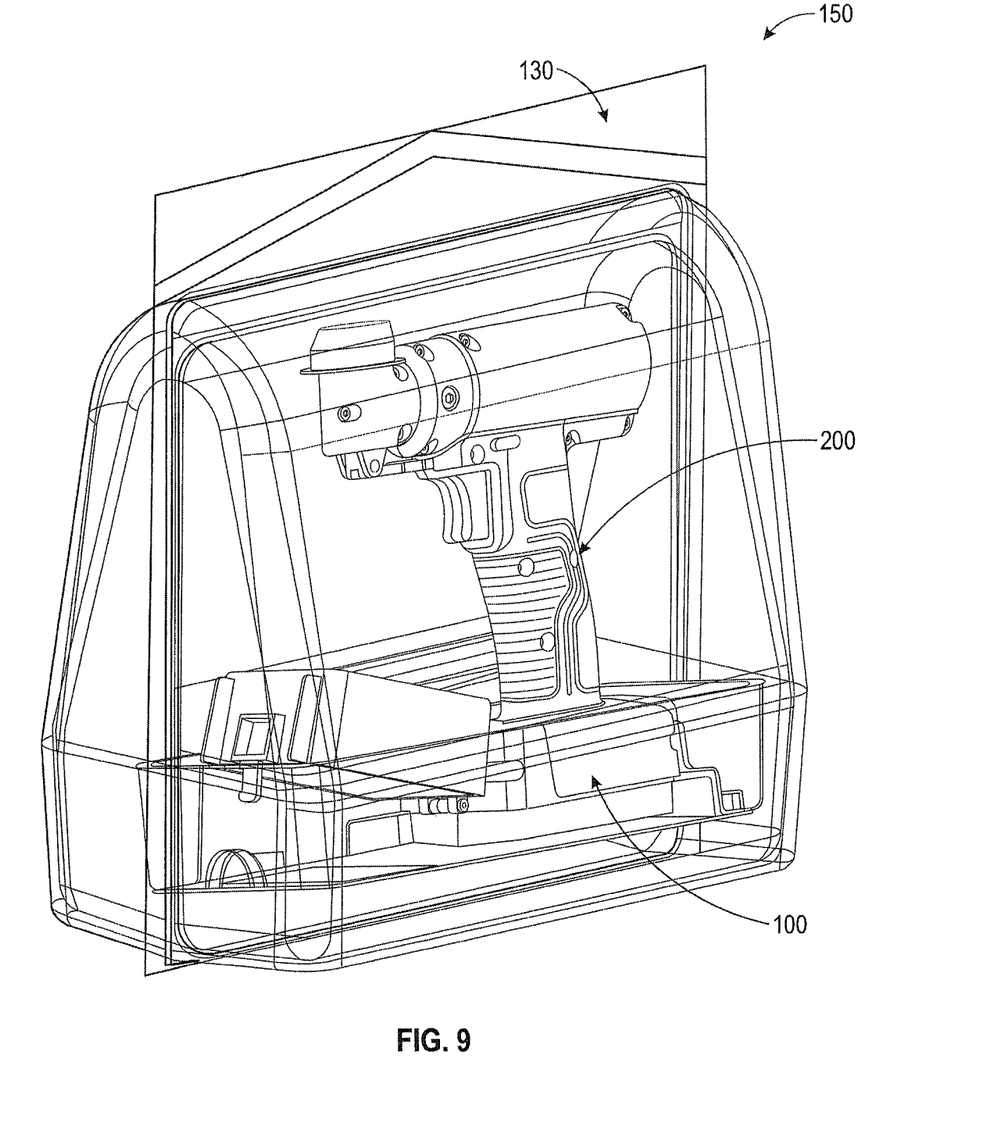
FIG. 9 is a representative ISO view illustrating the entire packaging system with the tool, the inner packaging tray assembly and an outer sterile shield "bag", as delivered to an end-user.

FIG. 9 illustrates a typical entire sterile battery powered medical device packaging system 150 with the tool 200, the packaging tray assembly 100 and an illustrative sterile shield outer transport "bag" 130. One of skill in the art would recognize that such sterile shield outer transport containers can frequently comprise one or more boxes, one or more plastic bags, or a combination of both, as deemed necessary by the manufacturer to guarantee sterile shipping and delivery to the end-user.

In some embodiments of the medical device packaging system, the tray assembly is configured from injection molded materials. In some embodiments, the exterior outer shield or transport packaging may be configured from injection molded materials.

In some embodiments of the medical device packaging system the tray assembly is configured from vacuum formed materials. In some embodiments, the exterior outer shield or transport packaging may be configured from vacuum formed materials.

In some embodiments, the exterior outer shield or transport packaging may be configured from polyethylene or similar plastic packaging materials.

In some embodiments of the medical device packaging system the tray assembly is configured from die cut materials.

In some embodiments, the exterior outer shield or transport packaging may be configured from die cut materials.

Provided herein is a method of sterile transfer of a non-sterile component to a sterile device in a sterile field comprising: providing a medical device packaging system comprising a packaging tray assembly having both sterile and non-sterile zones; providing a sterile medical device releasably secured within a sterile zone of the packaging tray assembly; wherein said medical device comprises a sterile receiver housing and sterile receiver housing cover; providing a non-sterile component configured for assembly to the sterile medical device within the sterile field; inserting said non-sterile component internally into a receiver housing opening of the sterile receiver housing through a non-sterile zone opening in the packaging tray assembly; closing the open receiver housing opening with the sterile receiver housing cover; and removing the sterile tool comprising the internally inserted non-sterile component from the packaging tray assembly in the sterile field.

Provided herein is a method of sterile transfer of a non-sterile component to a sterile device in a sterile field comprising: providing a medical device packaging system comprising a packaging tray assembly having both sterile and non-sterile zones; providing a sterile medical device releasably secured within a sterile zone of the packaging tray assembly; wherein said medical device comprises a sterile receiver housing and sterile receiver housing cover; providing a non-sterile component configured for assembly to the sterile medical device within the sterile field; inserting said non-sterile component internally into a receiver housing opening of the sterile receiver housing through a non-sterile zone opening in the packaging tray assembly; removing the sterile tool comprising the internally inserted non-sterile component from the packaging tray assembly in the sterile field; and closing the open receiver housing opening with the sterile receiver housing cover.

In some embodiments of the method, the non-sterile component is a battery.

In some embodiments of the method, said battery comprises: a disposable battery; a single use battery; a limited use battery; a rechargeable battery; or a recyclable battery.

In some embodiments of the method, the medical device comprises: a reusable power tool; a disposable power tool; a single use power tool or limited use power tool.

In some embodiments of the method, the packaging tray assembly having both sterile and non-sterile zones further comprises providing at least one sterile barrier shield, wherein said barrier shield is: releasable; removeable; hinged; or a combination thereof.

In some embodiments of the method, said sterile barrier shield provides an access port to a non-sterile zone in the packaging tray assembly.

In some embodiments of the method, the packaging tray assembly having both sterile and non-sterile zones further comprises providing at least one sterile barrier shield, wherein said barrier shield is non-releasable; or non-removeable.

In some embodiments of the method, the packaging tray assembly having both sterile and non-sterile zones further comprises providing retaining features within the sterile zone to releasably secure the sterile medical device during the insertion of said non-sterile component internally into the receiver housing opening of the sterile receiver housing.

While various embodiments of the present invention have been shown and described herein, it will be obvious to those skilled in the art that such embodiments are provided by way of example only. Numerous variations, changes, and substitutions may now occur to those skilled in the art without departing from the invention. It should be understood that various alternatives to the embodiments of the present disclosure described herein may be employed. It is intended that the following claims define the scope of the invention and that methods and structures within the scope of these claims and their equivalents be covered thereby.

What is claimed is:

1. A medical device packaging system comprising:
an outer package comprising:
an entire medical device;
a sterile tray assembly having a first sterile side, a second sterile side, a first sterile barrier comprising a sterile tray between the first and second sterile side and a second sterile barrier, the second sterile barrier being releasable over the second sterile side;
wherein the first sterile side, the second sterile side, the first sterile barrier and the second sterile barrier are all sterile when removed from the outer package,
wherein the first sterile side comprises a first sterile controlled zone within the tray assembly that is sterile when removed from the outer package and remains sterile when transferred to a surgical operating field,
wherein the second sterile side comprises a second controlled zone within the tray assembly that is initially sterile when removed from the outer package and later becomes a non-sterile controlled zone after releasing the second sterile barrier following insertion of a non-sterile battery into an originally sterile interior battery compartment within the second controlled zone;
wherein the first sterile side of said sterile tray assembly is releasably secured to a proximal exterior portion of the entire sterile medical device having a sterile device body, a sterile proximal battery housing, a sterile handle; and a sterile battery compartment cover in the first sterile controlled zone, and
wherein the originally sterile interior battery compartment of the proximal battery housing is accessible in the second controlled zone through an opening in the second sterile barrier and a first opening in the sterile tray over an opening in the internal sterile battery compartment of the proximal battery housing, such that a sterile person can handle the entire sterile medical device with the tray assembly in a vertical orientation from the first sterile side of the sterile tray assembly within the sterile operating field and present it the internal sterile battery compartment of the proximal battery housing to a non-sterile person in a controlled manner from within the sterile operating field,
wherein said non-sterile person can insert a non-sterile battery through the opening in the second sterile barrier and the first opening in the first sterile barrier into the internal sterile battery compartment of the proximal battery housing from an area outside of the sterile operating field, thus making the internal battery compartment non-sterile, while the proximal exterior portion of the entire sterile medical device remains isolated and sterile behind the first sterility barrier on the first side of the tray assembly, and
wherein the second sterile barrier can then be released from over the second sterile side to expose a second opening proximal to the first opening in the first sterile barrier of the sterile tray assembly.

2. The medical device packaging system of claim 1, further comprising a plurality of securing features comprising:
a first releasable securing feature on the first side of the sterile tray assembly for securing the proximal exterior portion of the sterile medical device in a manner which keeps the sterile medical device body, the sterile proximal battery housing and the sterile handle on the first sterile side of the tray assembly and the interior battery compartment opening on the second sterile side of the tray assembly;

a second releasable securing feature on the first side of the sterile tray assembly which captures an edge of the sterile outer battery compartment cover configured to hold said cover open and secure on the first sterile side of the tray assembly within the first controlled sterile zone of the packaging assembly;

wherein, following the release of the second sterile barrier, the entire sterile medical device can be removed backward and upward in a vertical motion from the tray assembly toward the first controlled sterile zone such that the battery compartment cover can be closed in a sterile fashion to seal the now non-sterile interior battery compartment with the sterile battery compartment cover by the sterile person within the sterile operating field while maintaining sterility of the entire exterior of the medical device.

3. The medical device packaging system of claim 1, further comprising:

capture features on the tray assembly and the second sterile barrier which capture and contain the second sterile barrier over the second sterile side of the sterile tray.

4. The medical device packaging system of claim 1, further comprising:

a flexible hinge feature on the second sterile barrier attached to the first sterile barrier of the tray assembly which allows tray assembly to be opened from the second side, without detaching the second sterile barrier from the tray assembly.

5. The medical device packaging system of claim 2, further comprising:

a sterile compartmental cavity of the tray assembly on the first side of the sterile tray configured to secure the entire sterile medical device, having compartmental securement features which into the sterile compartmental cavity of the tray assembly to secure the sterile proximal battery housing of the proximal sterile medical device in place.

6. The medical device packaging system of claim 5, further comprising:

releasable capture features on the sterile tray assembly configured to hold the entire sterile medical device and configured to allow intentional removal of the sterile medical device by a user.

7. The medical device packaging system of claim 2, comprising the releasable second sterile barrier:

wherein the second sterile barrier is completely removable from the sterile tray assembly.

8. The medical device packaging system of claim 1, wherein said sterile tray assembly is configured from injection molded materials.

9. The medical device packaging system of claim 1, wherein said sterile tray assembly is configured from vacuum formed materials.

10. The medical device packaging system of claim 1, wherein said sterile tray assembly is configured from die cut materials.

11. The medical device packaging system of claim 4, further comprising:

at least a capture or lip feature to prevent the sterile battery compartment cover from falling into the second controlled zone, and, or at least one hinge feature to prevent the second sterile barrier from falling into the sterile operating field.

* * * * *